US012708299B2

(12) United States Patent
Lee et al.

(10) Patent No.: US 12,708,299 B2
(45) Date of Patent: Aug. 18, 2026

(54) DIRECT ELECTRON TRANSFER GLUTAMATE BIOSENSOR USING PLATINUM NANOPARTICLE AND CARBON NANOTUBES

(71) Applicant: Purdue Research Foundation, West Lafayette, IN (US)

(72) Inventors: Hyowon Lee, West Lafayette, IN (US); Tran N.H. Nguyen, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 1211 days.

(21) Appl. No.: 17/625,262

(22) PCT Filed: Jul. 6, 2020

(86) PCT No.: PCT/US2020/040910
§ 371 (c)(1),
(2) Date: Jan. 6, 2022

(87) PCT Pub. No.: WO2021/007167
PCT Pub. Date: Jan. 14, 2021

(65) Prior Publication Data
US 2022/0218246 A1 Jul. 14, 2022

Related U.S. Application Data
(60) Provisional application No. 62/871,152, filed on Jul. 7, 2019.

(51) Int. Cl.
*A61B 5/1486* (2006.01)
*A61B 5/145* (2006.01)
(Continued)

(52) U.S. Cl.
CPC ...... *A61B 5/14865* (2013.01); *A61B 5/14507* (2013.01); *A61B 5/14546* (2013.01); *C01B 32/168* (2017.08); *C01B 2202/06* (2013.01)

(58) Field of Classification Search
CPC ............ A61B 5/14865; A61B 5/14507; A61B 5/14546; A61B 5/1486; C01B 32/168; C01B 2202/06; C12N 11/08; C12Q 1/005
See application file for complete search history.

(56) References Cited

U.S. PATENT DOCUMENTS

| | | | |
|---|---|---|---|
| 4,663,230 | A | 5/1987 | Tennent |
| 2003/0032001 | A1 | 2/2003 | Broderick et al. |

(Continued)

OTHER PUBLICATIONS

Maity and Kumar (Year: 2019).*

(Continued)

*Primary Examiner* — Justin Xu
(74) *Attorney, Agent, or Firm* — Brown Rudnick LLP; Adam M. Schoen

(57) ABSTRACT

A direct electron transfer amperometric biosensor fabricated using direct write printing technology for in vivo electrochemical monitoring, such as monitoring of neurotransmitters and other biomarkers, e.g., in traumatic spinal cord injury. The biosensor is fabricated by immobilizing glutamate oxidase on nanocomposite electrodes made of platinum nanoparticles, multiwall carbon nanotubes and a conductive polymer on a flexible substrate.

20 Claims, 12 Drawing Sheets

(51) Int. Cl.
*C01B 32/168* (2017.01)
*C12N 11/08* (2020.01)
*C12Q 1/00* (2006.01)

(56) References Cited

U.S. PATENT DOCUMENTS

2007/0026440 A1* 2/2007 Broderick .......... A61B 5/14735 205/777.5
2010/0285514 A1 11/2010 Claussen et al.
2015/0024289 A1* 1/2015 Wang .................. H01M 4/9041 429/525
2015/0053564 A1* 2/2015 Harttig ............... G01N 27/3272 204/403.14
2020/0381637 A1* 12/2020 Zhang .................. H10K 77/111

OTHER PUBLICATIONS

Pan and Arnold (Year: 1996).*
Bethune, 1993, Cobalt-catalysed growth of carbon nanotubes with single-atomic-layer walls, Nature, 363:605-607.
Iijima, 1991, Helical microtubules of graphitic carbon, Nature, 354:56-58.
Iijima, 1993, Single-shell carbon nanotubes of 1-nm diameter, Nature 363(6430):603-605.
International Seach Report and Written Opinion issued in International Application No. PCT/US2020/040910, date of mailing: Oct. 16, 2020, 26 pages.
Kouvetakis, 1994, Novel Synthetic Routes to Carbon-Nitrogen Thin Films, Chem. Mater., 6:811-814.
Kratschmer, 1990, Solid C60: a new form of carbon, Nature, 347(6291):354-358.
Kroto, 1985, C60:Buckminsterfullerene, Nature, 318:-162-163.
Mintmire, 1992, Are Fullerene Tubules Metallic? Physical Review Letters, 68:631-634.
Monthioux, 2006, Who should be given the credit for the discovery of carbon nanotubes?, Carbon 44(9):1621-1623.
Nguyen, 2019, Facile Fabrication of flexible glutamate biosensor using direct writing of platinum nanoparticle-based nanocomposite ink, Biosensors and Bioelectronics, 131(31):257-266.
Oberlin, 1976, Filamentous Growth of Carbon Through Benzene Decomposition, J. Crystal Growth, 32:335-349.
Oku, 2000, Microstructure analysis of CN-base nanocage materials by high-resolution electron microscopy, Diamond and Related Materials, 9(3-6):906-910.
Smith, 1998, Encapsulated C60 in carbon nanotubes, Nature, 396:323-324.
Smith, 2000, Formation mechanism of fullerene peapods and coaxial tubes: a path to large scale synthesis, Chemical Physica Letters, 321:169-174.
Stoner, 2011, Graphenated carbon nanotubes for enhance electrochemical double layer capacitor performance, Applied Physics Letters, 99:183104-1.
Yang, 2020, Recent Developments of Flexible and Stretchable Electrochemical Biosensors, Micromachines, 11(3):243, 33 pages.
Yin, 2003, Unique Single-Crystalline Beta Carbon Nitride Nanorods, Adv. Mater., 15(21): 1840-1844.
Yu, 2011, Carbon Nanotube with Chemically Bonded Graphene Leaves for Electronic and Optoelectronic Applications, J. Phys, Chem. Lett., 2:1556-1562.
Zhong, 2010, Synthesis of high nitrogen doping of carbon nanotubes and modeling the stabilization of filled DAATO@CNTS (10,10) for nanoenergetic materials, J. Physics and Chemistry Solids, 71:134-139.

* cited by examiner

| Element | Wt % Average |
|---|---|
| C | 41.21 |
| O | 29.01 |
| Al | 2.07 |
| Si | 25.86 |
| S | 0.36 |
| Pt | 1.49 |
| Total | 100 |

DIRECT ELECTRON TRANSFER GLUTAMATE BIOSENSOR USING PLATINUM NANOPARTICLE AND CARBON NANOTUBES

RELATED APPLICATIONS

This Application is a 35 U.S.C. § 371 national phase application of PCT/US2020/040910, filed Jul. 6, 2020, which claims the benefit of and priority to U.S. Provisional Patent Application Ser. No. 62/871,152, filed Jul. 7, 2019, the content of each of which is incorporated by reference herein in its entirety.

TECHNICAL FIELD

This Application relates to direct electron transfer glutamate biosensors featuring platinum nanoparticles and carbon nanotubes.

BACKGROUND

Spinal cord injury (SCI) is one of the three most life-threatening traumas along with traumatic brain injury and stroke. It is a devastating and debilitating condition that affects approximately 2.5 million people worldwide. At least 17,000 people in the United States suffer from SCI every year, and almost 300,000 Americans live with SCI, often confined to wheelchairs and experiencing severe mobility issues. SCI patients and their caretakers suffer significant economic and social burdens. The Center for Disease Control estimated that $9.7 billion is spent on SCI each year in the United States alone. SCI pathophysiology can be separated into two main phases: primary and secondary injuries. The primary injury occurs with the initial mechanical insult when the spinal cord is compressed or disrupted. The traumatic primary injury typically happens rapidly and unexpectedly; therefore, therapeutic intervention at this stage is often inaccessible and ineffective. The secondary injury, which immediately follows the initial damage, consists of a sequence of destructive physiological events that continues for days or even months due to edema, ischemia, inflammation, glutamate excitotoxicity, oxidative stress species, and delayed necrotic and apoptotic cell death (FIG. 1).

Glutamate excitotoxicity (GET), a pathology in which excessive glutamate causes neuronal damage and degeneration, is suspected as one of the main culprits behind secondary SCI. Despite extensive research, however, the mechanism behind and the extent of sustained high levels of extracellular glutamate remains unclear. A better understanding of GET following SCI may lead to a novel therapeutic intervention to suppress glutamate elevation that exacerbates the damage.

Currently, there are several non-invasive and invasive methods such as nuclear resonance imaging or microdialysis to quantify glutamate levels in vivo. However, existing techniques often suffer from low sensitivity and poor spatiotemporal resolution, which has severely limited understanding of this dynamic event. Electrochemical implantable microsensor arrays represent a promising alternative due to relatively fast response time and precise positioning. Using conventional MEMS techniques, several groups have developed microscale biosensors for glutamate. Table 1 presents selected current electrochemical platforms for measurement of glutamate. However, most MEMS-based glutamate biosensors are rigid, expensive and time consuming to fabricate.

There remains a need to provide a highly sensitive and specific amperometric glutamate detection system in vivo.

SUMMARY

Systems and methods of the present disclosure provide an implantable biosensor for detecting glutamate excitotoxicity in vivo. Exemplary biosensors may comprise a nanocomposite electrode comprising a plurality of platinum nanoparticles; a plurality of multiwall carbon nanotubes; and a conductive polymer on a flexible substrate. The nanocomposite electrode comprises glutamate oxidase on the biosensor surface and is operable to detect direct electron transfer from L-glutamate by printing an amperometric response signal with an applied potential.

Biosensors may be fabricated using direct write printing technology and used for in vivo electrochemical monitoring. Biosensors can be fabricated by immobilizing glutamate oxidase on nanocomposite electrodes made of platinum nanoparticles, multi-wall carbon nanotubes and a conductive polymer on a flexible substrate. The sensor allows for measurement of extracellular dynamics of neurotransmitters and other biomarkers in traumatic SCI via direct electron transfer. Highly sensitive and specific amperometric glutamate detection can be achieved at −200 mV with the systems and methods. In bench-top evaluation, biosensors have shown a linear range from 5 to 600 μM, with a sensitivity of 12.81±1.182 nA $\mu M^{-1}$ mm', and a detection limit of 14 μM (n=3). The biosensors can be highly specific to L-glutamate without any interference from other electroactive species present in typical biological fluid. Furthermore, the glutamate biosensors disclosed herein exhibit good repeatability, reproducibility, and stability.

Aspects include an implantable biosensor comprising a nanocomposite electrode that may comprise a plurality of platinum nanoparticles; a plurality of multiwall carbon nanotubes; and a conductive polymer on a flexible substrate. The nanocomposite electrode may comprise glutamate oxidase on its surface and can be operable to detect L-glutamate via direct electron transfer in response signal to an applied potential.

Implantable biosensors may be operable to detect L-glutamate by amperometric response signal to the applied potential. In certain embodiments, they may be operable to quantify L-glutamate by the amperometric response signal. The conductive polymer may comprise poly(3,4-ethylenedioxythiophene) polystyrene sulfonate (PEDOT:PSS) and the flexible substrate may comprise one or more of an Ecoflex polydimethylsiloxane (PDMS) composite and a liquid crystal polymer sheet (LCP).

In certain embodiments, the implantable biosensor may include a layer of Nafion on its surface upon which the glutamate oxidase enzyme is immobilized. The platinum nanoparticles can be about 1% wt, the multiwall carbon nanotubes can be about 1% wt and the substrate Ecoflex can be about 16% wt. The applied potential can be between about 650 mV and about −200 mV. Implantable biosensors according to certain embodiments may be sensitive to L-glutamate concentration of about 12.85 nA $\mu M^{-1}$ $mm^{-2}$.

In certain aspects, the methods can include detecting L-glutamate in a subject by providing a biosensor as described above, applying a potential to the biosensor, reading an amperometric response signal generated from direct electron transfer on the nanocomposite electrode surface in response to the applied potential, and detecting L-Glutamate in the subject based on the amperometric response signal.

In certain embodiments, the biosensor may be implanted in the subject and the subject may be human. The subject may have experienced a traumatic spinal cord injury (SPI). Methods may include measuring a level of L-glutamate in the subject based on the amperometric response signal. In certain embodiments, methods may further include determining a risk of traumatic spinal cord injury (SPI) based on the level and treating the subject based on the level.

The biosensors may be about 4-6 times more sensitive to L-Glutamate concentration compared to $H_2O_2$-mediated detection methods.

DETAILED DESCRIPTION

Figure 1:
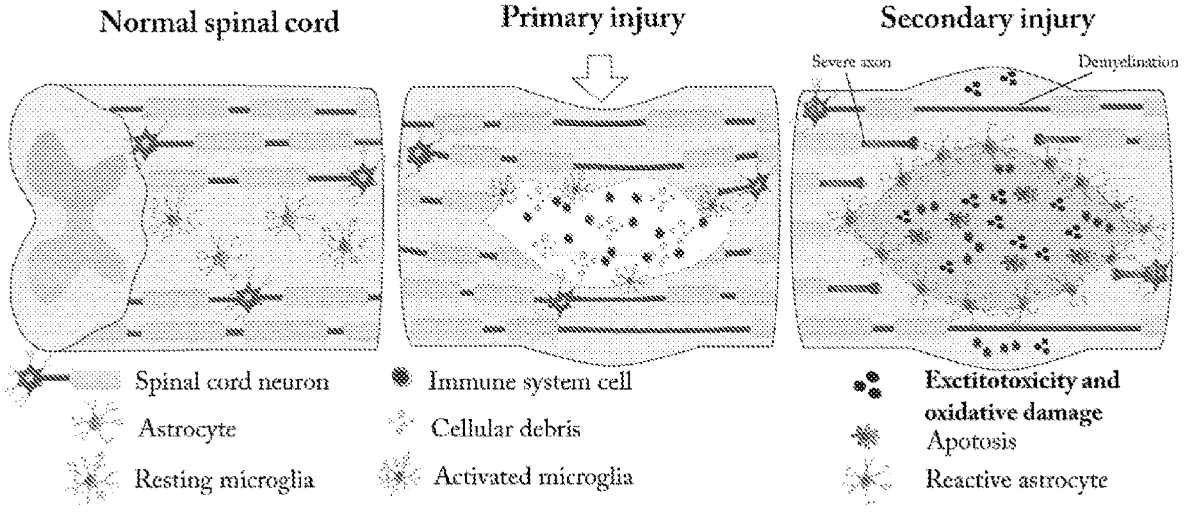
FIG. 1 diagrams the progression of SCI through different phases, including normal spinal cord state, primary injury and secondary injury.

While the concepts of the present disclosure are illustrated and described in detail in the figures and the description herein, results in the figures and their description are to be considered as exemplary and not restrictive in character; it being understood that only the illustrative embodiments are shown and described and that all changes and modifications that come within the spirit of the disclosure are desired to be protected.

Unless defined otherwise, the scientific and technology nomenclatures have the same meaning as commonly understood by a person in the ordinary skill in the art pertaining to this disclosure.

Glutamate excitotoxicity is a pathology in which excessive glutamate can cause neuronal damage and degeneration. It has also been linked to secondary injury mechanism, which further aggravates the damage in traumatic spinal cord injury (SCI). To date, there are various conventional bioanalytical techniques to characterize glutamate level in vivo; however, these techniques feature low spatiotemporal resolution, which has severely limited understanding of this dynamic event. Herein is disclosed a direct electron transfer amperometric biosensor fabricated using direct write printing technology towards in vivo electrochemical monitoring. The biosensor can be fabricated by immobilizing glutamate oxidase on nanocomposite electrodes made of platinum nanoparticles, multi-wall carbon nanotubes and a conductive polymer on a flexible substrate. The sensor allows for measurement of extracellular dynamics of neurotransmitters and other biomarkers in traumatic SCI. Highly sensitive and specific amperometric glutamate detection can be achieved at −200 mV with systems and methods disclosed herein. In bench-top evaluation, the biosensors have shown a linear range from 5 to 600 μM, with a sensitivity of 12.81±1.182 nA $\mu M^{-1}$ $mm^{-2}$, and a detection limit of 14 μM (n=3). The biosensors can be highly specific to L-glutamate without any interference from other electroactive species present in typical biological fluid. Furthermore, the glutamate biosensors disclosed herein exhibit good repeatability, reproducibility, and stability.

In recent years, printed electronics have attracted a great attention for rapid production of low-cost, large-area, flexible devices. Specifically, much effort has been focused on using printing techniques for developing devices for biological, medical, and optical applications. There are existing reports of creating flexible amperometric glutamate and other biosensors using screen-printing and ink-jet printing. However, these processing techniques require additional support by underlying substrate, as well as necessary mask/pattern for printing, while producing low-aspect ratio pattern. Direct writing techniques offer an alternative way to generate device patterns in which the architecture and the composition can be controlled through computer-controlled translation stage. Using direct writing, a number of functional materials can be deposited to construct structure with high aspect ratio and spanning features on to a multitude of surfaces.

The present disclosure provides a low-cost but highly sensitive implantable glutamate biosensor that can be prepared using omnidirectional printing technique with nanocomposite material. The microscale electrochemical biosensor can be fabricated with low manufacturing costs and may be used to monitor the fluctuation of extracellular glutamate over the course of SCI to shed additional insight on disease progression and recovery. Using nanocomposite ink that consists of platinum nanoparticle (PtNPs), multi-walled carbon nanotubes (MWCNT), and conductive polymer, poly (3,4-ethylenedioxythiophene) polystyrene sulfonate (PEDOT:PSS), and EcoFlex, a direct electron transfer (DET) type glutamate biosensor can be formed that is more sensitive and selective than conventional microfabricated electrochemical glutamate biosensors (Table 1).

TABLE 1

Different types of glutamate biosensors

| Type of Electrode | Area ($mm^2$) | Fabrication method | Sensitivity (nA $\mu M^{-1} mm^{-2}$) | Permselective membrane |
|---|---|---|---|---|
| Pt/Ir/Metal wires | 0.1830 | Pt-Iridium wire | 0.54 | Nafion |
| Carbon Fibre | 0.0095 | Carbon fiber | 0.36 | Nafion |
| Glassy carbon | 7.0680 | Electrodeposition | 2.10 | Nafion |
| Platinum | 0.0491 | Pt cylinder prepared from Pt wire | 0.80 | polypyrrole-PPY |
| Platinum | 0.0491 | Platinum disk | 0.32 | poly (o-phenylenediamine)-PPD |
| Platinum/Chtosan | 8.0425 | Pt cylinder prepared from Pt wire | 0.85 | poly (o-phenylenediamine)-PPD |
| Clark type oxygen electrode (Pt) | 0.7854 | Clark type oxygen electrode | 0.11 | Teflon |
| CNT composite electrode | 7.0000 | Glassy carbon | 0.10 | NA-low oxidation potential |
| Pt electrode | 0.0040 | MEMS | 0.62 | Nafion |
| Pt electrode | 0.0075 | MEMS | 0.95 | m-phenylenediamine-mPD |
| Pt wire/MWCNT | 0.7800 | Electrodeposition | 3.84 | Polypyrrole OPP |
| PtNPs/Au nano array | 0.2000 | Electrodeposition | 0.11 | Nafion |
| Pt | 0.0050 | MEMS | 1.26 | Nafion-Polypyrrole-PPY |
| Platinum disk | 0.0491 | Pt cylinder prepared from Pt wire | 0.71 | Poly (o-phenylenediamine)-PPD |
| Pt electrode | 0.0040 | MEMS | 1.93 | Nafion |
| MWCNT/AuNP/CHIT | 36.000 | Electrodeposition | 1.55 | NA-low oxidation potential |
| Pt electrode/Silicon | 0.0284 | MEMS | 0.03 | m-phenylenediamine-mPD |
| Pt/Silicon-based | 0.0075 | MEMS | 7.47 | Nafion |
| Prussian Blue/Carbon fiber electrode | 0.00007 | Carbon fiber | 0.35 | Poly-o-phenylenediamine-PoPD |
| Carbon nanofibers | 98300 | Carbon nanofibers | 0.18 | NA-low oxidation potential |
| PtNPs/MWCNT/PETOD:PSS | 0.0314 | Direct Writing | 12.85 | NA-low oxidation potential |

DET-type enzymatic biosensors operate at low potential range close to the redox potential of the enzyme itself and transfer electron directly between the active center of redox enzyme and the electrode surface. Because the DET occurs at a lower potential, it provides greater selectivity against other electroactive chemicals such as ascorbic acid and uric acid without the need for perm-selective layers.

Glutamate oxidase (GluOx), which is a highly sensitive enzyme used as the basis for many glutamate biosensors, is a type of flavoprotein enzyme with FAD (flavin adenine dinucleotide)/$FADH_2$ as the redox prosthetic group. It is generally difficult for GluOx-$FADH_2$ to be directly oxidized electrochemically due to electrically insulating protein shell. Even when enzyme is immobilized on the electrode surface, the distance between the electrode surface and the redox center surpasses critical electron tunneling distance.

In various embodiments, DET-type glutamate biosensors comprising PtNPs nanocomposite ink are disclosed that can be manufactured using low-cost scalable fabrication techniques.

Nanoparticles are typically between 1 and 100 nanometers (nm) in diameter and can exhibit different properties than found in larger particles of the same substance. Platinum nanoparticles can be useful in enzymatic sensors by providing electrocatalytic properties while avoiding some of the challenges presented by oxidation of standard platinum surfaces. In various embodiments, other nanoparticle materials may be used in electrodes including gold, silver, palladium, other noble metals, and alloys thereof.

Nanotubes are nanometer-scale tube-like structures. Exemplary nanotubes are carbon nanotubes, silicon nanotubes, boron nitride nanotubes, or inorganic nanotubes (i.e., nanotubes formed of metal oxides, or group III-Nitrides).

In certain embodiments, the nanotubes are carbon nanotubes, which are described for example in Monthioux et al. (Carbon 44 (9): 1621, 2006), Oberlin et al. (Journal of Crystal Growth 32 (3): 335-349, 1976), Endo et al. (Carbon 37 (11): 1873, 2002), Izvestiya wet al. (Metals. 1982, #3, pp. 12-1'7), Tennent (U.S. Pat. No. 4,663,230), Iijima et al. (Nature 354 (6348): 56-58, 1991), Mintmire et al., (Phys. Rev. Lett. 68 (5): 631-634, 1992), Bethune (Nature 363 (6430): 605-607, 1993), Iijima et al., (Nature 363 (6430): 603-605, 1993), Krätschmer et al. (Nature 347 (6291): 354-358, 1990), and Kroto et al. (Nature 318 (6042): 162-163, 1985), the content of each of which is incorporated by reference herein in its entirety for its disclosure regarding same.

Carbon nanotubes (CNTs) are allotropes of carbon with a cylindrical nanostructure. Carbon nanotubes are members of the fullerene structural family. Their name is derived from their long, hollow structure with the walls formed by one-atom-thick sheets of carbon, called graphene. These sheets are rolled at specific and discrete ("chiral") angles, and the combination of the rolling angle and radius determines the nanotube properties; for example, whether the individual nanotube shell is a metal or semiconductor. Carbon nanotubes are categorized as single-walled nanotubes (SWNTs) and multi-walled nanotubes (MWNTs).

Most single-walled nanotubes (SWNT) have a diameter of close to 1 nanometer, with a tube length that can be many millions of times longer. The structure of a SWNT can be conceptualized by wrapping a one-atom-thick layer of graphite called graphene into a seamless cylinder. The way the graphene sheet is wrapped is represented by a pair of indices (n,m). The integers n and m denote the number of unit vectors along two directions in the honeycomb crystal lattice of graphene. If m=0, the nanotubes are called zigzag nanotubes, and if n=m, the nanotubes are called armchair nanotubes. Otherwise, they are called chiral.

In preferred embodiments, biosensors of the invention use multi-walled nanotubes (MWNT). MWNTs consist of multiple rolled layers (concentric tubes) of graphene. There are two models that can be used to describe the structures of multi-walled nanotubes. In the Russian Doll model, sheets of graphite are arranged in concentric cylinders, e.g., a (0,8) single-walled nanotube (SWNT) within a larger (0,17) single-walled nanotube. In the Parchment model, a single sheet of graphite is rolled in around itself, resembling a scroll of parchment or a rolled newspaper. The interlayer distance in multi-walled nanotubes is close to the distance between graphene layers in graphite, approximately 3.4 Å. The Russian Doll structure is observed more commonly. Its individual shells can be described as SWNTs, which can be metallic or semiconducting. Because of statistical probability and restrictions on the relative diameters of the individual tubes, one of the shells, and thus the whole MWNT, is usually a zero-gap metal.

As used herein, the term carbon nanotubes includes carbon nanobuds, which are a combination of carbon nanotubes and fullerenes. In carbon nanobuds, fullerene-like buds are covalently bonded to the outer sidewalls of the underlying carbon nanotube. This hybrid material has useful properties of both fullerenes and carbon nanotubes. In particular, they have been found to be exceptionally good field emitters. In composite materials, the attached fullerene molecules may function as molecular anchors preventing slipping of the nanotubes, thus improving the composite's mechanical properties.

As used herein, the term carbon nanotubes also includes graphenated CNTs, which are a hybrid that combines graphitic foliates grown along the sidewalls of multiwalled or bamboo style CNTs. Graphenated CNTs are described for example in Yu et al. (J. Phys. Chem. Lett. 13 2 (13): 1556-1562, 2011), and Stoner et al. (Appl. Phys. Lett. 18 99 (18): 183104, 2011), the content of each of which is incorporated by reference herein in its entirety.

As used herein, the term carbon nanotubes also includes doped carbon nanotubes, such as nitrogen doped carbon nanotubes (Kouvetakis et al., Chemistry of Materials 6 (6): 811, 1994; Zhong et al., Journal of Physics and Chemistry of Solids 71 (2): 134, 2010; Yin et al., Advanced Materials 15 (21): 1840, 2003; and Oku et al., Diamond and Related Materials 9 (3-6): 906, 2000; the contents of each of which is hereby incorporated by reference); and a carbon peapod, which is a hybrid carbon material which traps fullerene inside a carbon nanotube (Smith et al., Nature 396: 323-324, 1998; and Smith et al., Chem. Phys. Lett. 321: 169-174, 2000; the content of each of which is incorporated herein by reference).

In preferred embodiments, the biosensor substrate comprises an Ecoflex, polydimethylsiloxane (PDMS) composite substrate or a liquid crystal polymer sheet (LCP) but any suitable substrate material can be used. See, e.g., Yang, X. and Cheng, H., 2020, Recent Developments of Flexible and Stretchable Electrochemical Biosensors, Micromachines (Basel) 11(3): 243, incorporated herein by reference.

In certain embodiments, methods may include providing treatment to a patient based on a detected level of L-glutamate. Levels above a certain threshold may be indicative of an increased risk of glutamate excitotoxicity and associated SPI. Such treatments may include the administration of glutamate antagonists such as estrogen, ginsenoside, progesterone, simvastatin, and memantine.

EXAMPLES

Example 1: Fabrication of PtNPs Nanocomposite Biosensor

FIG. 2*a* shows a fabrication process of a flexible glutamate biosensor using omnidirectional printing on an elastomeric Ecoflex polydimethylsiloxane (PDMS) composite substrate or on a liquid crystal polymer sheet (LCP). Ecoflex was used to increase the flexibility of the substrate and to minimize sensor induced damage to the surrounding spinal cord tissue. PtNPs nanocomposite ink was used to define the working and the counter electrodes, as well as the conductive traces. The silver/silver chloride (Ag/AgCl) ink was used as the reference electrode and the contact pads. PDMS was then printed over the device to insulate the biosensor leaving only the working, reference, and the counter electrodes exposed for electrochemical activity.

Figure 2:
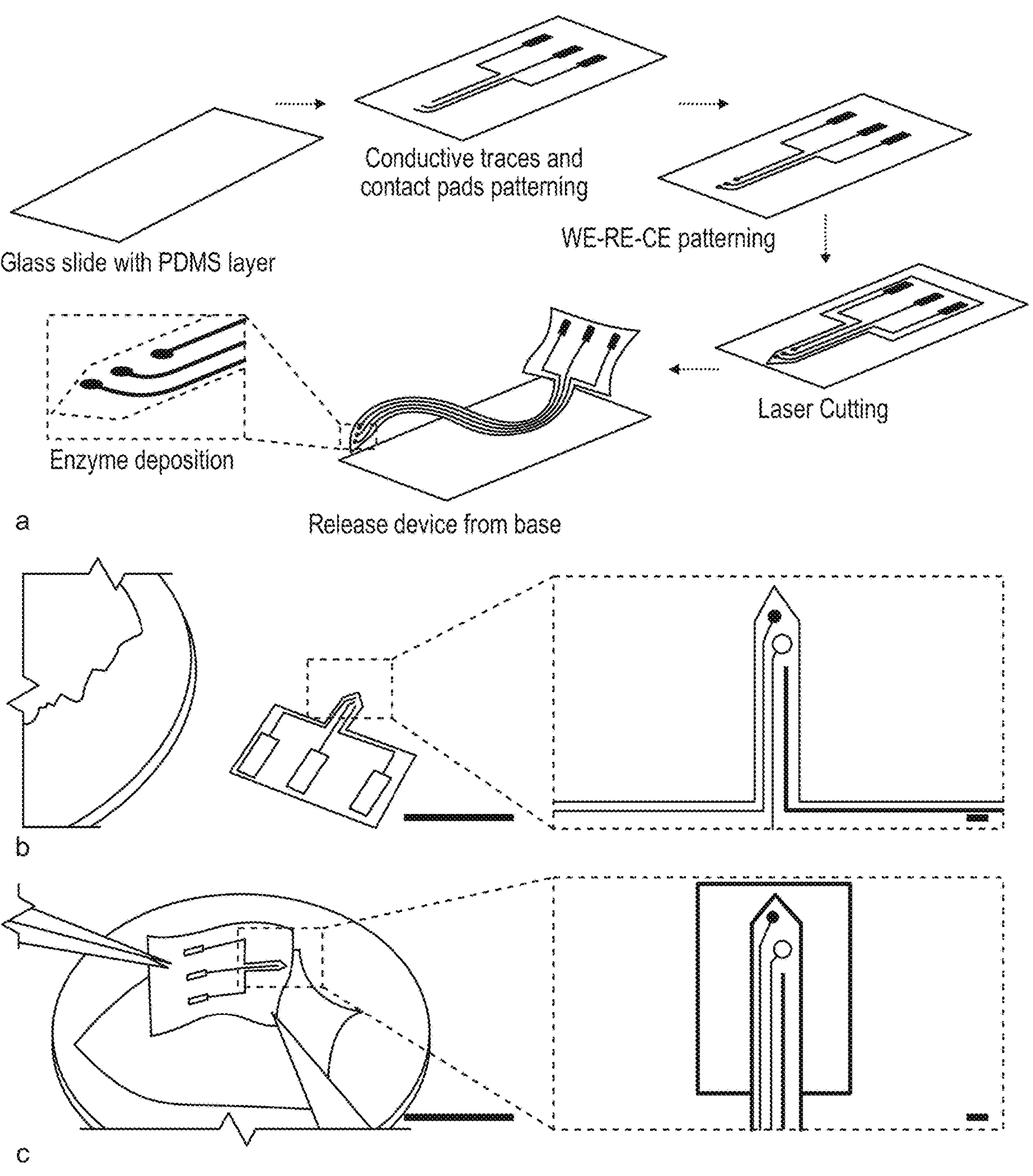
FIG. 2: (a) Schematic of fabrication process of platinum nanoparticle (PtNPs)-nanocomposite-based glutamate biosensor on a polydimethylsiloxane (PDMS) substrate. (b) Photograph of a flexible micro-glutamate biosensor on PDMS substrate (scale bar 5 mm and 200 μm). (c) Photograph of a flexible micro-glutamate biosensor on liquid crystal polymer (LCP) sheet (scale bar 5 mm and 200 μm).

Following the printing of the electrodes, the working electrode was coated either with an enzyme matrix to complete the glutamate biosensor, or with a layer of Nafion before coating with enzyme matrix to improve selectivity (FIG. 2). FIG. 2*b* presents the complete device with PDMS substrate, which was laser cut and released from the support surface. FIG. 2*c* shows a sample of another glutamate biosensor, which was printed directly on a micromachined LCP using maskless lithography.

Example 2: Surface Characterization of PtNPs Nanocomposite

Figure 3:
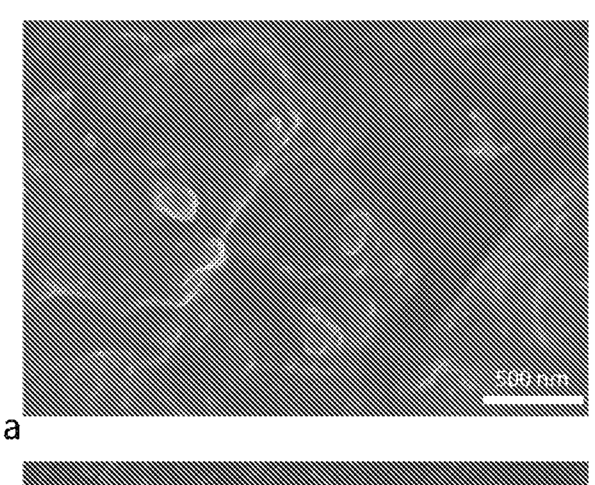
FIG. 3: (a-b) Scanning electron microscopy micrograph of PtNPs nanocomposite on aluminum substrate with different magnifications. (c) energy-dispersive x-ray spectroscopy (EDX) pattern of fabricated PtNPs nanocomposite.
Figure 3:
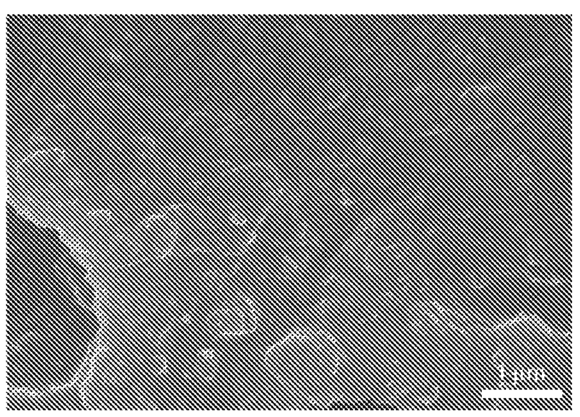
Figure 3:
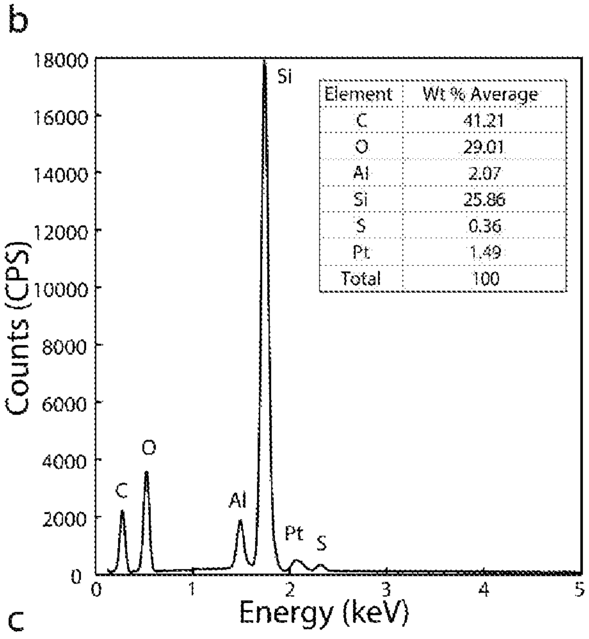

The surface morphology of the PtNPs nanocomposite was observed by field-emission scanning electron microscopy (FESEM, S-4800, Hitachi, Japan). The elemental composition was determined using an energy dispersive Xray spectroscopy (EDX) attached to the FESEM system. FIGS. 3*a* and *b* show FESEM images of the resulting PtNPs nanocomposite ink at different magnifications. The nanocomposite electrode appeared to have a rough surface morphology, which is likely due to a combination of MWCNT and PtNPs in PEDOT:PSS and Ecoflex. The rough surface texture is expected to contribute to a higher sensor sensitivity by facilitating DET and better immobilization of GluOx.

The EDX spectrum presented in FIG. 3*c* provides the typical signal of PtNPs in the nanocomposite. For EDX characterization, the PtNPs nanocomposite electrodes were fabricated on an aluminum surface, which explains the appearance of Al in the EDX spectrum.

Quantitative analysis taking the average value of reading at four difference spots on the sample surface indicated that the weight percent of platinum was approximately 1.49%, which corresponds closely with the weight percentage used to make the nanocomposite ink.

Example 3: Cyclic Voltammetry of Nanocomposite Electrodes

The cyclic voltammetry was utilized to acquire qualitative information on various electrochemical reactions. The electrocatalytic activity of the nanocomposite was evaluated in 0.01 M phosphate buffered saline (PBS, pH 7.0). FIG. 4*a* shows the cyclic voltammograms (CV) of PtNPs nanocomposite electrode compared to MWCNT-PEDOT: PSS and PEDOT: PSS electrodes. The CV of PEDOT: PSS electrode displays a rectangular shape, which suggests a more capacitor-like behavior. The same trait is observed for MWCNT-PEDOT: PSS, in which the electrochemical response is determined by the electrical double layer formation associated with high surface area of the MWCNT and porous structure of PEDOT: PSS. The MWCNT-PEDOT: PSS composite electrode displayed higher current density values compared to PEDOT: PSS alone, in agreement with literature regarding PEDOT: PSS modified with carbon materials. A more distinct CV can be seen when PtNPs are mixed with MWCNT and PEDOT, exhibiting clear characteristics of Pt electrodes with the highest current responses compared to the other electrodes.

The use of PtNPs together with CNT is known to enhance the detection of $H_2O_2$, a byproduct of enzymatic oxidation. As such, the electrochemical response of PtNPs nanocomposite electrode was expected to be superior to the other polymer electrodes. FIG. 4*b* shows the amperometric responses of different electrodes against $H_2O_2$ in 0.01 M PBS (pH 7.0) at 650 mV (n=3). After 20 minutes of settling, 20 μM $H_2O_2$ was added in successive portions to elicit current responses. The PtNPs nanocomposite electrodes exhibited the highest electrocatalytic activity towards $H_2O_2$. The calibration plot showed a well-defined linear response with a high sensitivity of 12.52±1.323 nA $\mu M^{-1}$ $mm^{-2}$ for PtNPs nanocomposite compared to sensitivities of 0.49±0.098 $\mu M^{-1}$ $mm^{-2}$ and 0.068±0.013 nA $\mu M^{-1}$ $mm^{-2}$ for MWCNT-PEDOT: PSS and PEDOT: PSS electrodes, respectively (FIG. 4*b*). Table 2 summarizes the performance of different electrodes (i.e., sensitivity, detection limit, and working range).

TABLE 2

Performance of nanocomposite electrodes

| Type of electrode | Analyte | Applied potential (mV) | Sensitivity (nA $\mu M^{-1} mm^{-2}$) | Linear range (μM) | Detection limit (μM) |
|---|---|---|---|---|---|
| PEDOT:PSS | $H_2O_2$ | 650 | 0.068 ± 0.013 | — | 44.96 |
| MWCNT/PEDOT:PSS | $H_2O_2$ | 650 | 0.493 ± 0.098 | — | 7.745 |
| PtNPs/MWCNT/PEDOT:PSS | $H_2O_2$ | 650 | 12.52 ± 1.323 | — | 2.816 |
| PtNPs/MWCNT/PEDOT:PSS | Glutamate | 650 | 1.992 ± 0.151 | 5-700 | 7.347 |
| PtNPs/MWCNT/PEDOT:PSS | Glutamate | −200 | 12.81 ± 1.182 | 5-600 | 14.17 |

Example 4: Electrochemical Detection of Glutamate Via DET

Figure 5:
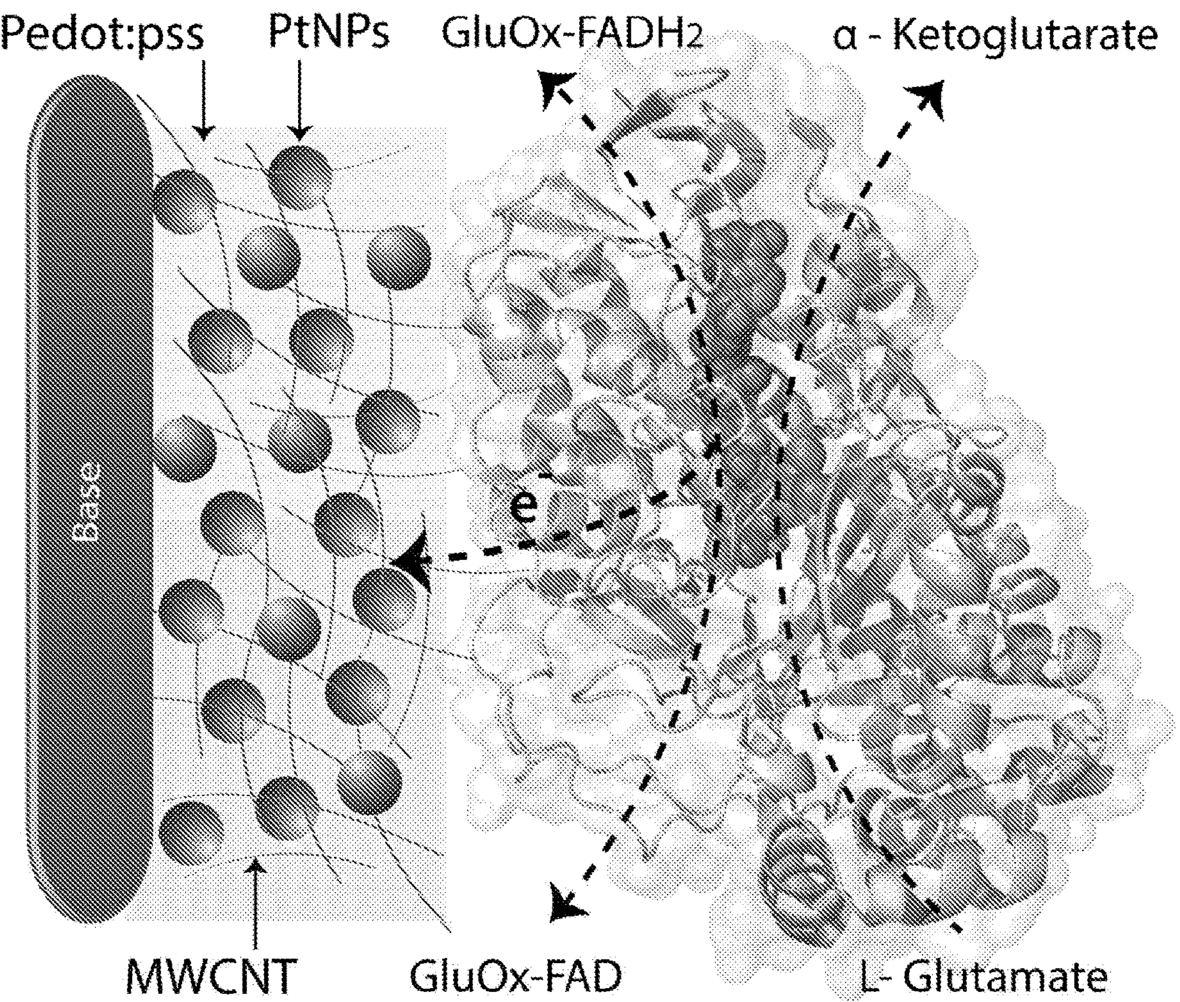
FIG. 5 is an illustration of a direct electron transfer (DET) mechanism of Pt-NPs nanocomposite biosensor for L-glutamate. The nanoscale feature is thought to provide a direct coupling to the FAD redox center (green) of glucose oxidase (GluOx) enzyme. The GluOx crystal structure is from *Streptomyces* sp. X-119-6 (PDB accession code: 2E1M).
Figure 6:
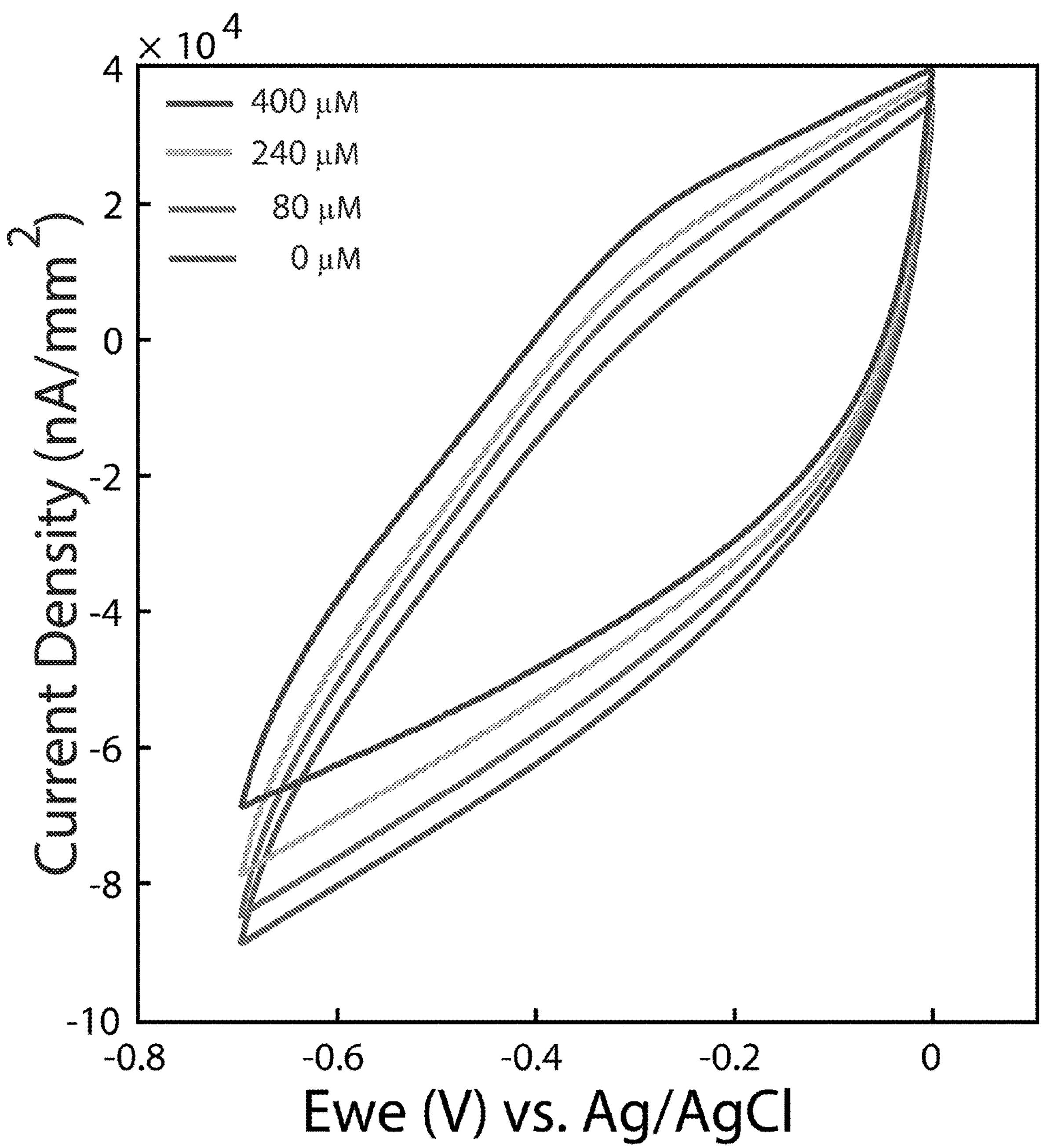
FIG. 6 shows cyclic voltammetry obtained for Pt-NPs nanocomposite glutamate biosensor in $N_2$ saturated 0.01 M PBS (pH=7.0) containing different concentrations of glutamate. Scan rate: 100 mV $s^{-1}$. Note the increasing oxidation current and decreasing reduction current with increasing concentration of L-glutamate. In a deoxygenated environment, the oxygen-mediated catalysis of $H_2O_2$ is not expected to occur, which suggests the biosensor response to glutamate may be due to DET.

The nanoscale features of the electrode surface provided by the PtNPs and MWCNT is hypothesized to provide a direct coupling of the sensor surface to the GluOx/FAD redox center. FIG. 5 shows an illustration of hypothesized DET mechanism between GluOx and PtNPs nanocomposite biosensor to detect L-glutamate concentration. In this case, GluOx/FAD is first reduced to GluOx/$FADH_2$ by L-glutamate. Then, GluOx/$FADH_2$ is re-oxidized to GluOx/FAD by the PtNPs nanocomposite electrode in a cyclic catalytic reaction. The sequence of reactions (R1 and R2) represents the DET process without the need for any redox mediator (e.g., $O_2$), which is required to generate and reduce $H_2O_2$ to detect glutamate using conventional first-generation glutamate biosensors. In $N_2$-saturated PBS, the cyclic voltammetry (CV) of PtNPs nanocomposite biosensor conjugated with GluOx (GluOx-PtNPs) is shown to be still responsive to glutamate with increase in GluOx/$FADH_2$ oxidation current and decrease in GluOx/FAD reduction current (FIG. 6), which suggests a DET-mediated glutamate detection.

$$\text{L-glutamate+GluOx/FAD - - - }\alpha\text{-ketoglutarate+GluOx/FADH}_2 \quad \text{(R1)}$$

$$\text{GluOx/FADH}_2\text{ - - - GluOx/FAD+2H}^+\text{+2}e^- \quad \text{(R2)}$$

Conversely, in an aerobic environment, the oxidation of GluOx/$FADH_2$ can also be achieved using oxygen as the electron acceptor (R3). Therefore, CV measurement of GluOx-PtNPs nanocomposite biosensor was conducted in both $N_2$-saturated and air-saturated PBS to investigate the effect of oxygen on GluOx/$FADH_2$ oxidation compared to DET (See FIG. 7B). The PtNPs biosensor that was not functionalized with GluOx exhibited similar redox peaks regardless of oxygen level (See FIG. 7A). However, PtNPs-based glutamate biosensor demonstrated a large cathodic current in the presence of more oxygen that can be attributed to O2 reduction, which is electrochemically catalyzed by the GluOx/$FADH_2$.

$$\text{GluOx/FADH}_2\text{+O}_2\text{ - - - GluOx/FAD+H}_2\text{O}_2 \quad \text{(R3)}$$

Figure 7:
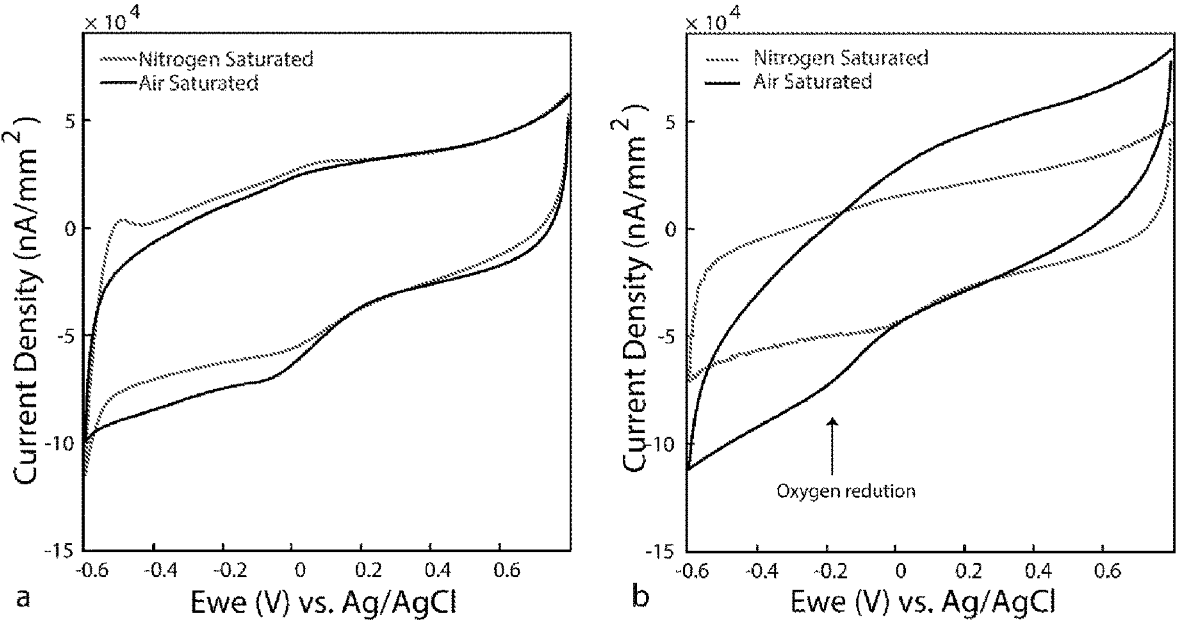
FIG. 7: a. Cyclic voltammetry obtained for bare PtNPs nanocomposite biosensor in $N_2$-saturated and air-saturated 0.01 M PBS (pH 7.0). b. Cyclic voltammetry obtained for GluOx conjugated PtNPs nanocomposite biosensor in $N_2$-saturated and air-saturated 0.01 M PBS (pH 7.0). Note the large oxygen reduction peak with GluOx in an oxygenated environment, which corresponds with reduction of $H_2O_2$ (R3).

FIG. 7*b* shows cyclic voltammetry data obtained for GluOx conjugated PtNPs nanocomposite biosensor in $N_2$-saturated and air-saturated 0.01 M PBS (pH 7.0). Note the large oxygen reduction peak with GluOx in an oxygenated environment, which corresponds with reduction of $H_2O_2$ (R3).

Example 5: Glutamate Detection Via 11202 Mediator Vs. DET

Figure 4:
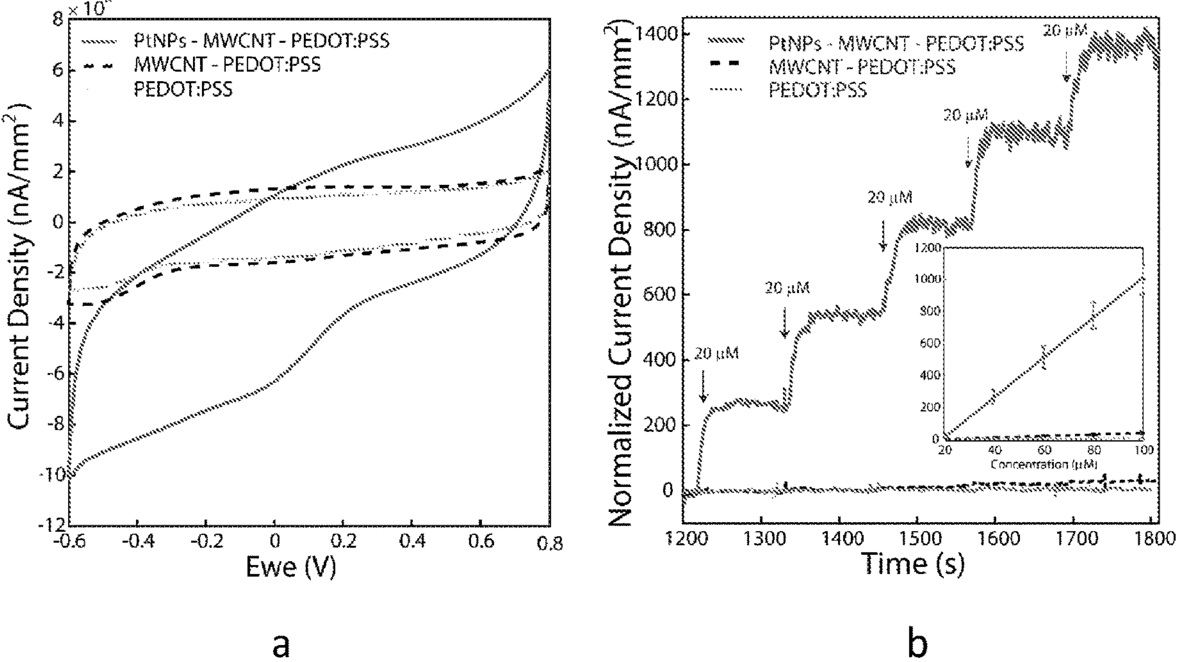
FIG. 4: (a) Cyclic voltammetry obtained for composite biosensor in 0.01 M phosphate-buffered saline (PBS) (pH 7.0) for different types of materials. Scan rate=100 mV $s^{-1}$. (b) Amperometric curve of different concentrations of $H_2O_2$ in 0.01 M PBS solution (pH 7.0) of PtNPs nanocomposite; multi-walled carbon nanotubes and conductive polymer, poly(3,4-ethylenedioxythiophene) polystyrene sulfonate (MWCNTPEDOT: PSS) and poly(3,4-ethylenedioxythiophene) polystyrene sulfonate (PEDOT:PSS) printing electrode at applied potential of 650 mV. Inset is the corresponding calibration curve of response current versus the concentration of $H_2O_2$.

Many first generation glutamate biosensors are based on the detection of the $H_2O_2$, a byproduct produced during the glutamate oxidation reaction. In the presence of oxygen, GluOx catalyzes successive reactions of L-glutamate to form $H_2O_2$, which can be oxidized at the electrode as shown in the equations (R4 and R5). As shown in FIG. 4, the PtNPs nanocomposite exhibited prominent electrocatalytic activity toward $H_2O_2$, which meant such electrodes could serve as a first-generation electrochemical platform for detection of L-glutamate via an oxidase-based mechanism.

Figure 8:
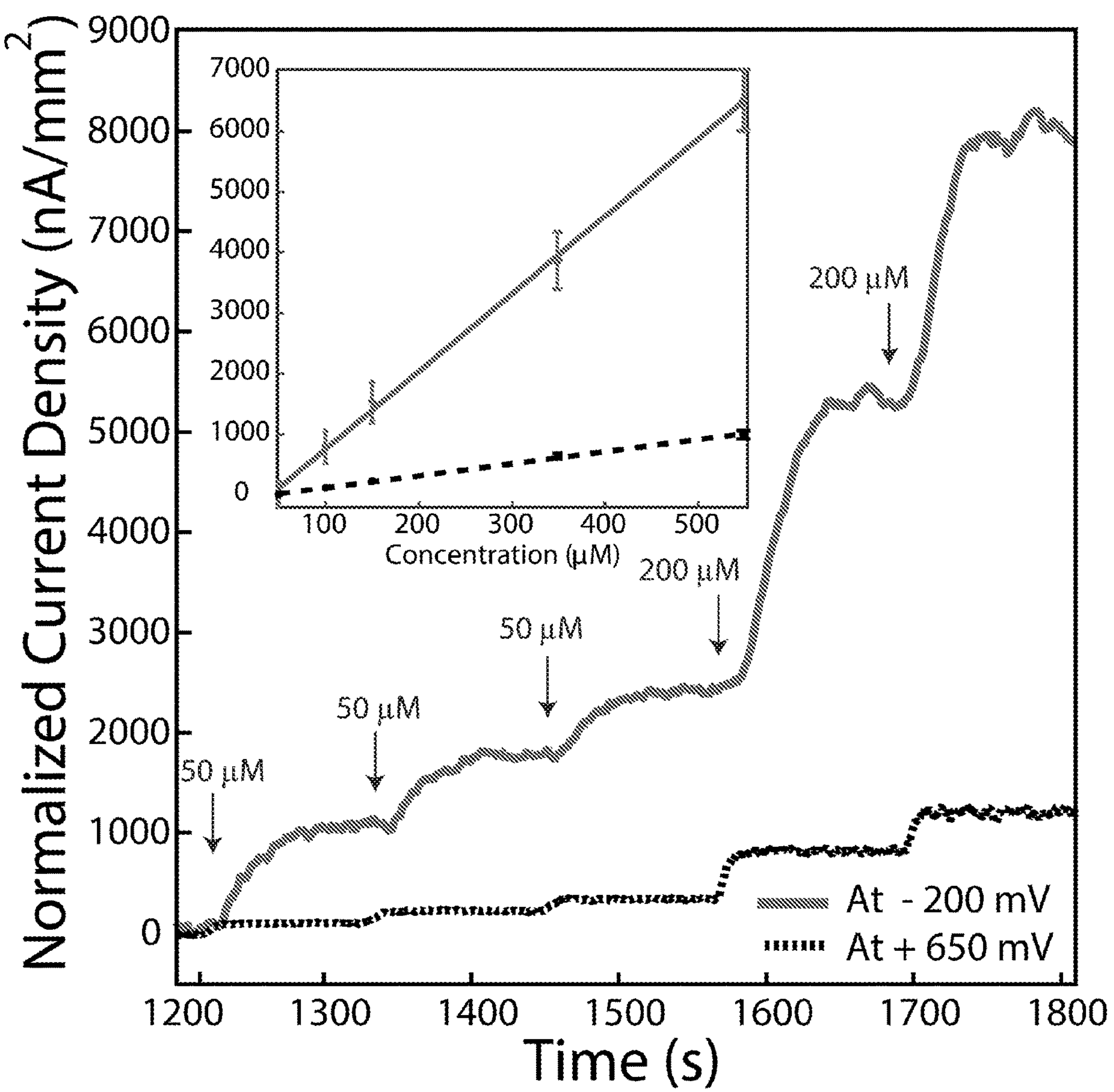
FIG. 8 shows amperometric i-t curve of different concentrations of L-glutamate in 0.01 M PBS solution (pH 7.0) of GluOx/PtNPs nanocomposite at −200 mV and GluOx/Nafion/PtNPs nanocomposite at 650 mV. Inset is the corresponding calibration curve of response current versus the concentration of L-glutamate.

To demonstrate the indirect detection of L-glutamate, a thin-layer of Nafion was drop casted over the nanocomposite working electrodes (n=3). FIG. 8 shows the amperometric response of the biosensor under aerobic conditions, demonstrating the oxidation current of $H_2O_2$ produced in R4 and R5. The calibration plot shows a linear kinetic reaction with a sensitivity of 1.992±0.151 nA $\mu M^{-1}$ $mm^{-2}$ of GluOx/Nafion/PtNPs nanocomposite toward L-glutamate.

$$\text{L-glutamate+H}_2\text{O+O}_2\text{ - - - }\alpha\text{-ketoglutarate+NH}_3\text{+H}_2\text{O}_2 \quad \text{(R4)}$$

$$\text{H}_2\text{O}_2\text{+2H++2}e\text{- - - - 2H}_2\text{O} \quad \text{(R5)}$$

Next, the performance of GluOx-PtNPs biosensor (n=3) was evaluated using chronoamperometry at −200 mV to demonstrate DET-based glutamate detection (FIG. 8). As expected, each addition of L-glutamate solution resulted in change in current. The linear calibration plot shows a linear relationship between current density and L-glutamate concentration, which is common in enzymatic kinetic reaction. The sensitivity for DET-based glutamte detection (12.805±1.182 nA $\mu M^{-1}$ $mm^{-2}$) was significantly greater than that of $H_2O_2$-mediated indirect glutamate detection.

Example 6: Additional Evidence for DET

Figure 9:
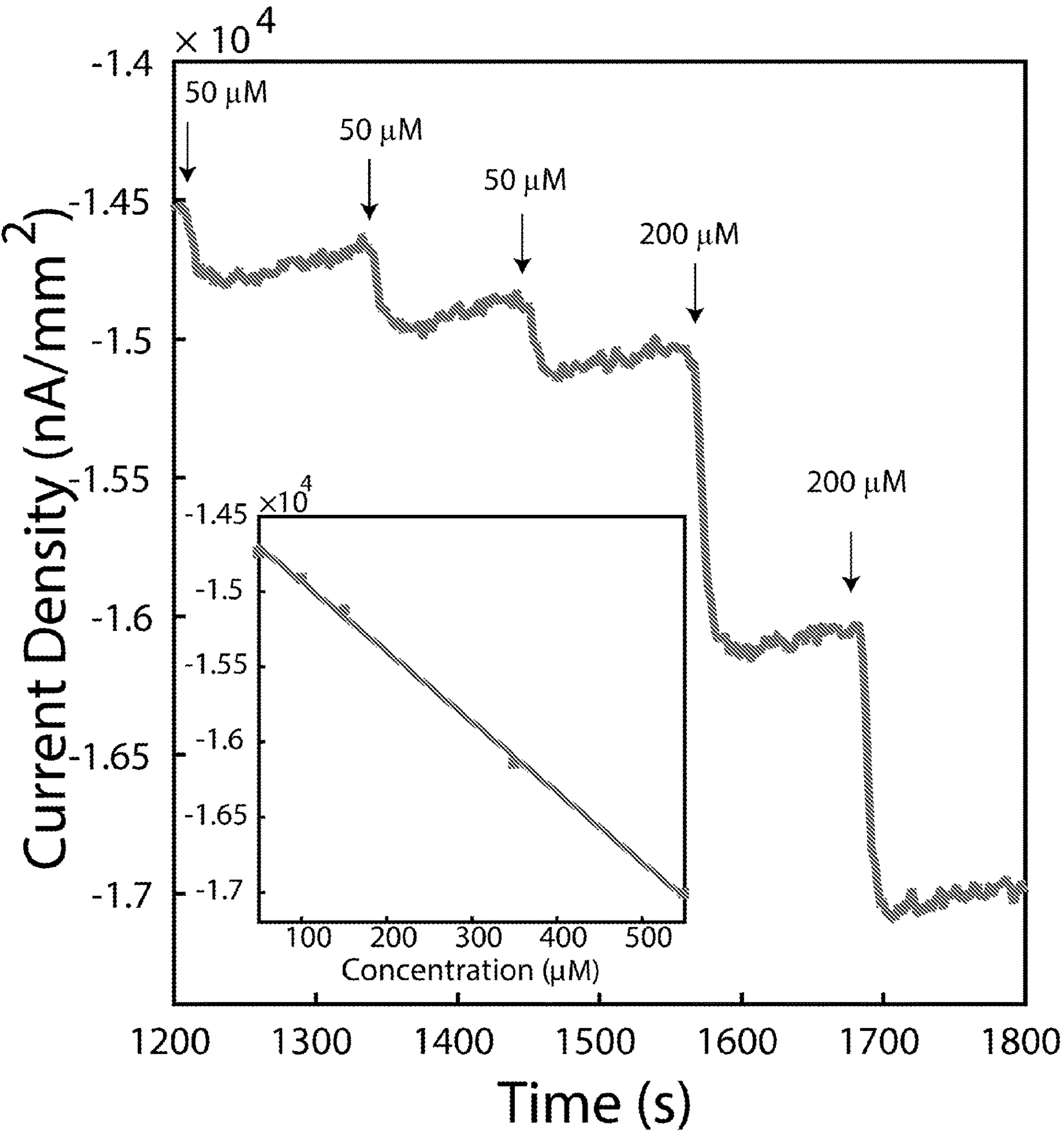
FIG. 9 shows an amperometric response to successive addition of $H_2O_2$ in 0.01 M PBS solution (pH 7.0) of PtNPs nanocomposite biosensor at the applied potential of 200 mV. Inset is the corresponding calibration curve of response current versus the concentration of $H_2O_2$.

To further demonstrate that the GluOx-PtNPs biosensor functions via DET, the electrocatalytic behavior of the electrode for reducing $H_2O_2$ at a negative potential was characterized. FIG. 9 shows a typical i-v response of the Pt-NPs nanocomposite upon successive addition of $H_2O_2$ into stirring 0.01 M PBS (pH 7.0) at an applied potential of −200 mV. The GluOx-PtNPs biosensor demonstrated an increase in reduction current as a function of added $H_2O_2$. This is in contrast to the amperometry data that showed a decrease in reduction current when L=glutamate was added (FIG. 8), which suggests that no $H_2O_2$ is being generated as described in R4 and R5.

Figure 10:
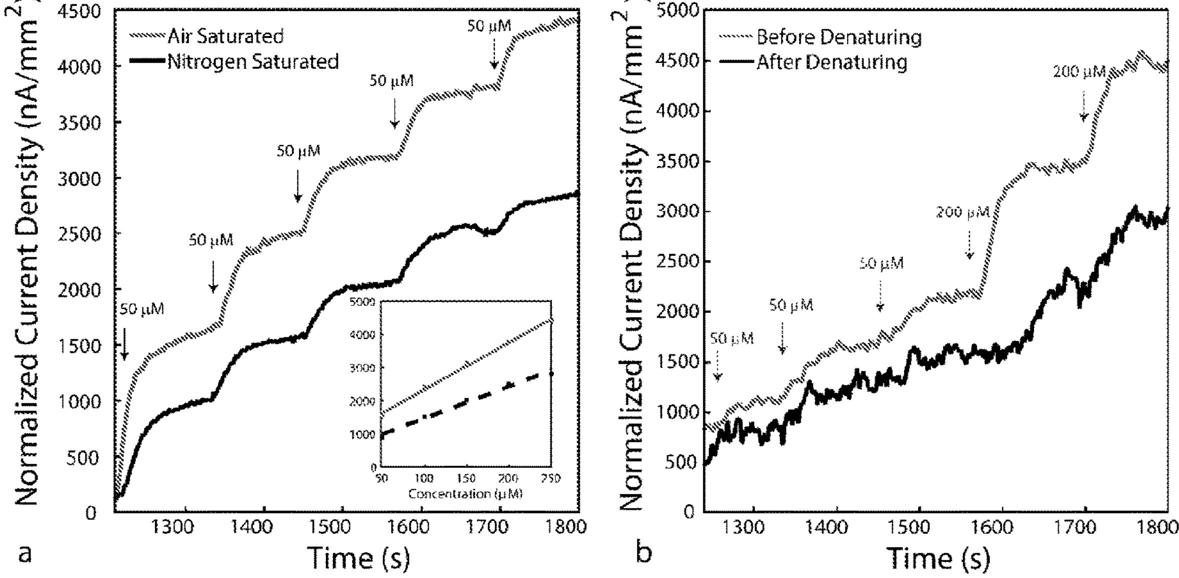
FIG. 10: a. Amperometric response of GluOx/PtNPs nanocomposite to L-glutamate in air-saturated and $N_2$-saturated 0.01 M PBS solution (pH 7.0). b. Amperometric response of GluOx/PtNPs nanocomposite to L-glutamate before and after denaturing the enzyme in 0.01 M PBS solution (pH 7.0).

As stated above, 02 can also oxidize GluOx/$FADH_2$ to GluOx/FAD (R3). Thus, it is necessary to assess the ability to detect glutamate in an 02-free environment as a confirmation that direct oxidation of $FADH_2$ was indeed performed by the electrode. An amperometric experiment at a constant potential of −200 mV was carried out by adding different concentrations of L-glutamate to the GluOx-PtNPs biosensor in both $N_2$-saturated and air-saturated PBS (FIG. 10*a*). The calibration plot shows high glutamate sensitivity of 14.208 nA $\mu M^{-1}$ $mm^{-2}$ in air-saturated PBS solution and 10.095 nA $\mu M^{-1}$ mm in $N_2$-saturated PBS. In an 02-free environment, the only way to recycle the reduced $FADH_2$ to FAD is via DET, which increases the oxidation current. Despite a slight reduction in sensitivity, the fact that the GluOx-PtNPs biosensor is still responsive to L-glutamate in $N_2$-saturated PBS provides more evidence for DET.

In order to test whether the electrochemical signal of the FAD cofactors may be possibly due to the dissociated FAD cofactor instead of DET, the amperometric response to glutamate of GluOx-PtNPs nanocomposite was compared to that of denatured GluOx. GluOx/PtNPs composite was briefly heated at 80° C. for 20 min to thermally denature the enzyme. FIG. 10*b* shows amperometric signal of a GluOx-PtNPs nanocomposite biosensor before and after denaturing the enzyme. As demonstrated above, the current from intact GluOx-PtNPs nanocomposite biosensor increased upon addition of L-glutamate. The current response was substantially attenuated after thermal denaturization, which may be attributed to the dissociated FAD cofactor.

Example 7: Selectivity, Reproducibility and Stability of GluOx-PtNPs Biosensor

Figure 11:
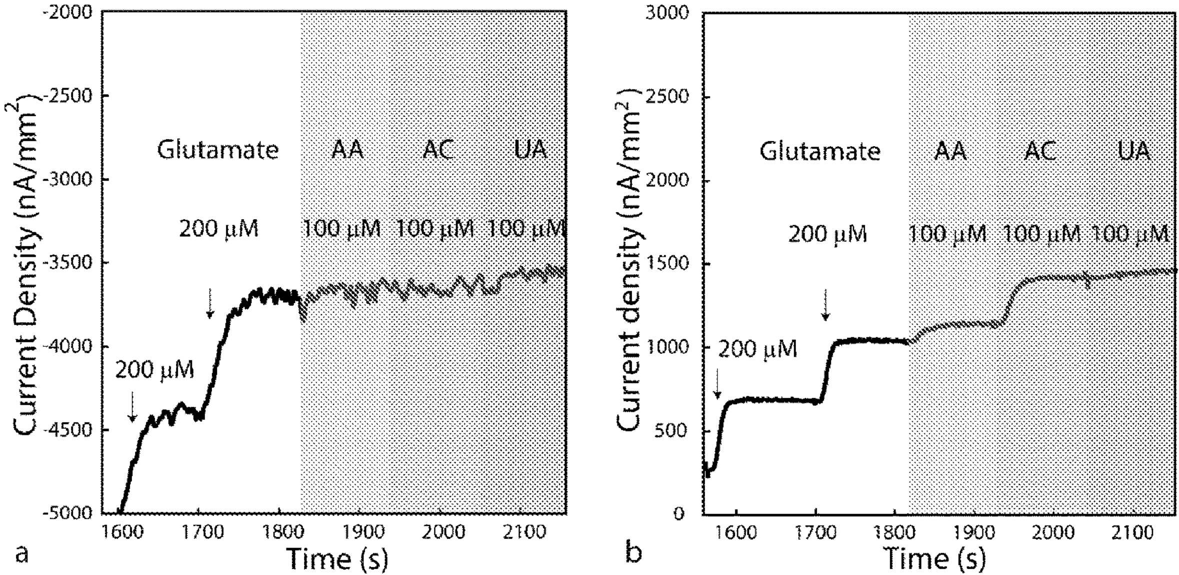
FIG. 11: a. Amperometric response of GluOx/PtNPs nanocomposite upon sequential addition of 200 μM L-glutamate, 100 μM of ascorbic acid, 100 μM of acetaminophen and 100 μM of uric acid into constantly stirred PBS solution at −200 mV applied potential. b. Amperometric response of GluOx/Nafion/PtNPs nanocomposite upon sequential addition of 200 μM glutamate, 100 μM of ascorbic acid, 100 M of acetaminophen and 100 μM of uric acid into constantly stirred 0.01 M PBS (pH 7.0) solution at 650 mV applied potential.

For successful in vivo electrochemical detection of glutamate, the biosensor must be highly selective against other electroactive species present in the body. FIG. 11*a* shows the DET response of a GluOx-PtNPs biosensor upon sequential addition of 200 μM L-glutamate, 100 of ascorbic acid, 100 μM of acetaminophen and 100 μM of uric acid into constantly stirred PBS solution at −200 mV applied potential while FIG. 11*b* shoes the DET response of a GluOx/Nafion/PtNPs biosensor upon sequential addition of 200 μM glutamate, 100 μM of ascorbic acid, 100 M of acetaminophen and 100 μM of uric acid into constantly stirred 0.01 M PBS (pH 7.0) solution at 650 mV applied potential. These common electroactive analytes did not affect the performance of GluOx-PtNPs nanocomposite biosensor even without a permselective membrane. Conversely, the GluOx-PtNPs biosensor was not able to effectively block the signals from AA and AC when indirect glutamate sensing is used (650 mV) even with Nafion permselective membrane.

Figure 12:
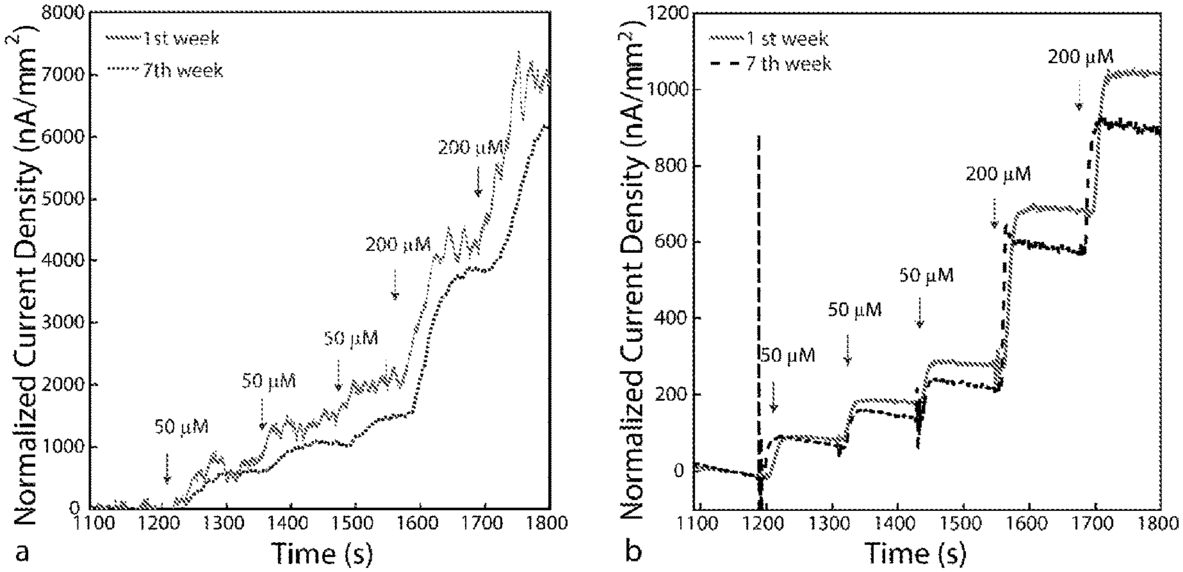
FIG. 12 shows an amperometric i-t curve of different concentrations of glutamate in 0.01 M PBS solution (pH 7.0) of a. GluOx/PtNPs nanocomposite at −200 mV and b. GluOx/Nafion/PtNPs nanocomposite 650 mV after 7 weeks.

The long-term stability of the developed sensor was also investigated by comparing the sensitivity of the biosensor before and after incubation at 4° C. in PBS for 7 weeks (n=3). FIG. 12 shows the amperometric response of GluOx-PtNPs nanocomposite biosensor at −200 mV before (FIG. 12*a*) and after (FIG. 12*b*) 7 weeks storage; after this period, the sensor still maintained 80.56±1.71% of its initial sensitivity. Similarly, the sensitivity of GluOx-PtNPs nanocomposite biosensor biased at 650 mV maintained 79.66±2.718% of the initial sensitivity. These results suggest a good storage stability of the GluOx-PtNPs nanocomposite biosensors.

As described herein, a nanocomposite ink that consists of PtNPs, MWCNT, PEDOT: PSS, and Ecoflex can be used to create a DET-type glutamate biosensor that may be used to probe the impact of glutamate excitotoxicity in spinal cord injury. This sensing mechanism is different from the first-generation glutamate biosensors, in which oxygen is needed, and glutamate detection relies on oxygen reduction and $H_2O_2$ oxidation in the presence of GluOx. It is also different from second-generation biosensors, in which a mediator is needed as a redox relay to shuttle electrons between enzyme and electrode. The DET activity of GluOx/PtNPs nanocomposite may be attributed to the nanostructures of PtNPs and MWCNTs that allows a more intimate contact with the redox centers inside the GluOx enzyme. In demonstration of similar DET mechanism using glucose oxidase, the shortening of electron tunneling distance was similarly hypothesized for the superior electrochemical performance of DET-type glucose biosensors. Metallic nanoparticles, in particular, have been used to establish a direct electrical pathway between redox centers of an enzyme and the electrode surface. CNTs are also known for their ability to improve electron transport when combined with metallic nanoparticles.

Finally, the conductive polymer, PEDOT: PSS, not only serves as the binder between the polymer matrix and nanofillers (PtNPs and MWCNT) and helps connect the particles together by π-π interaction, but its positively charged surface may also pull the negatively charged GluOx closer to the electrode surface to further decrease the tunneling distance and facilitate DET.

There are several advantages of a DET-based glutamate biosensor over other traditional $H_2O_2$-mediated L-glutamate biosensors. As demonstrated, the DET detection of glutamate showed a substantially higher sensitivity than the traditional enzymatic method (12.81±1.18 nA $\mu M^{-1}$ $mm^{-2}$ vs. 1.99±0.15 nA $\mu M^{-1}$ $mm^{-2}$ with good long-term stability (80% over 7 weeks). Compared to other amperometric glutamate biosensors, this work represents one of the highest sensitivity values to date (Table 1). Moreover, the low oxidation potential used to measure glutamate concentration allows for superior selectivity against other electroactive molecules found in the body without the addition of perm selective layer, which will facilitate in vivo measurements. Finally, the Pt-NPs nanocomposite ink allows for highly scalable and simple manufacturing of highly sensitive enzymatic glutamate biosensors.

Although these biosensors demonstrated good bench-top performance, the biosensors are preferably used to measure the level of glutamate in vivo. In certain embodiments, a biosensor array is contemplated to better characterize the change in glutamate concentration over time and space, which will improve the understanding of how glutamate excitotoxicity may propagate to exacerbate SCI.

Example 8: Experimental Reagents

PEDOT: PSS (5 wt. %, conductive screen printable ink), Nafion 117 solution (5 wt. % in mixture of water), platinum nanoparticles (<50 nm particle size) were obtained from Sigma Aldrich (St. Louis, MO). Carboxylic functionalized multi-walled carbon nanotube (MWCNT) were generously donated by Cheap Tubes Inc. (Grafton, Vermont). L-Glutamic acid, bovine serum albumin (BSA, min 96%), glutaraldehyde (50% in water), hydrogen peroxide (30%), 0.1 M phosphate buffer solution (PBS, pH 7), and dimethyl sulfoxide (DMSO) were obtained from Fisher Scientific (Walham, MA). Ascorbic acid and uric acid were purchased from Alfa Aesar (Thermo Fisher Scientific, Walham, MA). Glutamate oxidase (GluOx) from *Streptomyces*, with a rated activity of 25 units per mg protein was purchased from Cosmo Bio USA (Carlsbad, CA). PDMS (Sylgard 184) was purchased from Dow Corning (Midlant, MI). Water was purified by Milli-Q (Millipore, Bedford, MA).

Example 9: Preparation of PtNPs-MWCNTPEDOT: PSS Nanocomposite

To create the PtNPs nanocomposite, 30 mg of carboxylic functionalized MWCNT and 30 mg PtNPs were first mixed with 582.75 ml of DMSO in sonication bath for 2 h. The mixture then was added to 2000 mg PEDOT: PSS ink, and sonicated again for 10 min to re-disperse the nanomaterials. Finally, 520 mg Ecoflex was added and mixed using a homogenizer Ultra-Turrax T 25 (IKA, Wilmington, NC) at 10000 rpm for 10 h. The final mixture was dried in 60° C. in vacuum for 1 h to remove excess DMSO and to create desired viscosity for printing.

Example 10: Working Electrode Biofunctionalization

For Nafion-coated electrodes, 0.5 μl of 0.5 wt. % Nafion was dropped on the surface and dried at room temperature. For all working electrodes, the enzyme was immobilized using a solution of GluOx (100 U/ml), BSA (1 wt. %) and glutaraldehyde (0.15%). A 0.5 μl drop of solution was formed on a pipet tip, and was deposited on the working electrode under a microscope. Enzyme droplets were lowered on the working electrode.

This was repeated five times with each application consisting of four depositions on top of working electrode. Devices were placed at room temperature for 24 hours and then stored at 4° C. before first measurement. After first measurement, devices were stored in 0.01 M PBS (pH 7.0) at 4° C.

Example 11: Biosensor Fabrication and Electrochemical Evaluations

The fabrication process utilized omnidirectional printing of conductive inks using a commercial automated fluid dispensing system (Pro-EV 3, Nordson EFD, East Providence, RI). A custom glass capillary pipette with suitable μm diameter tip was fabricated to dispense microscale features. Electrochemical preparation of the sensors and in vitro experiments were performed using SP-200 potentiostat (Bio-logic USA, LLC, Knoxville, TN, USA). A conventional three-electrode cell was used in recording cyclic voltammetry. All electrochemical evaluations were performed in 0.1 PBS. To deoxygenate the PBS, highly pure $N_2$ (99.998%, Indiana Oxygen Company, Indianapolis, IN), was bubbled in for >1 h. To re-oxygenate the electrolyte, air was bubbled in for >1 h. All CVs were obtained using a scan rate of 100 mV All chronoamperometry was collected after 20 min of settling time.

Example 12: Micromachining of Implantable Biosensor

Two different micromachining techniques were used to fabricate the biosensor structure for implantation. First, 40-μm-thick PDMS substrate was prepared by spin-coating PDMS on a glass slide, which was coated with 500 nm of Parylene C to facilitate device release. PDMS was prepared by mixing 10:1 ratio w/w of base and curing agent. Thereafter, the PDMS substrate was cured in a vacuum oven at 60° C. for an hour. Desired electrode pattern was printed on the substrate and a femtosecond laser was ultilized to cut out desired structure.

A femtosecond laser (CARBIDE, Altos Photonics, USA) was used to cut the feature on the PDMS substrate at a microscale. The femtosecond laser operates with a wavelength of 1030 nm, a laser pulse duration of 290 fs, an output power of 2 W, a pulse repetition rate of 100 kHz, a scanning speed of 1 mm/s. A scanning path for laser cutting process was generated using a CAD drawing of the electrode pattern. The scanning path was additionally edited by considering the corner or end points of the pattern. As the points were manually selected by monitoring the pattern, the cutting lines were clearly achieved without any damage (FIG. 2*b*). The device was then released from the surface by submerging it in water.

The second type of device was fabricated on a liquid crystal polymer sheet (LCP) using a custom maskless photolithography setup. The commercially available LCP sheet (Ultralam 3850, Rogers corporation, Chandler, AZ, USA) has a thickness of 25 μm. A computer connected to a conventional home theater projector with a digital micromirror device (HD142X, Optoma, Fremont, CA, USA) was used to expose a desired pattern. The mask pattern was designed and projected using Microsoft PowerPoint. The exposure intensity was adjusted by modifying pattern color in the software.

The exposed LCP was etched by a deep reactive ion etcher (STS ICP Advanced Oxide Etch, Surface Technology System, Newport, United Kingdom) with 50 sccm of $O_2$ and 10 sccm of $SF_6$ at 2000 W in 2 mTorr for 7 min. After the desired structure was fabricated, devices were printed on the LCP pattern, and enzyme was immobilized to finish the L-glutamate biosensor (FIG. 2*c*).

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. An implantable biosensor comprising a nanocomposite electrode comprising:

a plurality of platinum nanoparticles in a nanocomposite ink;

a plurality of multiwall carbon nanotubes in the nanocomposite ink; and a conductive polymer in the nanocomposite ink, on a flexible substrate, wherein a greater amount of the conductive polymer is present in the nanocomposite ink than an amount of either or both of the plurality of platinum nanoparticles or the plurality of multiwall carbon nanotubes in the nanocomposite ink such that the conductive polymer forms a binder, while also decreasing tunneling distance, wherein said nanocomposite electrode comprises glutamate oxidase on its surface and detects L-glutamate via direct electron transfer in response signal to an applied potential.

2. The implantable biosensor of claim 1, which detects L-glutamate by amperometric response signal to the applied potential.

3. The implantable biosensor of claim 2, which quantifies L-glutamate by the amperometric response signal.

4. The implantable biosensor of claim 1, wherein said conductive polymer comprises poly(3,4-ethylenedioxythiophene) polystyrene sulfonate (PEDOT:PSS) and said flexible substrate comprises one or more of an Ecoflex polydimethylsiloxane (PDMS) composite and a liquid crystal polymer sheet (LCP).

5. The implantable biosensor of claim 4, wherein said platinum nanoparticles are 1% wt, said multiwall carbon nanotubes are 1% wt and said substrate Ecoflex PDMS composite is 16% wt.

6. The implantable biosensor of claim 1, further comprising a layer of Nafion on its surface upon which the glutamate oxidase enzyme is immobilized.

7. The implantable biosensor of claim 1, wherein said applied potential is between 650 mV and −200 mV.

8. The implantable biosensor of claim 1, which is sensitive to an L-glutamate concentration of 12.85 nA $\mu M^{-1}$ $mm^{-2}$.

9. A method of detecting L-glutamate in a subject, comprising:

providing a biosensor, wherein said biosensor comprises a nanocomposite electrode comprising:

a plurality of platinum nanoparticles in a nanocomposite ink;

a plurality of multiwall carbon nanotubes in the nanocomposite ink; and a conductive polymer in the nanocomposite ink, on a flexible substrate, wherein a greater amount of the conductive polymer is present in the nanocomposite ink than an amount of either or both of the plurality of platinum nanoparticles or the plurality of multiwall carbon nanotubes in the nanocomposite ink such that the conductive polymer forms a binder while also decreasing tunneling distance, wherein said nanocomposite electrode comprises glutamate oxidase on its surface; applying a potential to the biosensor;

reading an amperometric response signal generated from direct electron transfer on the nanocomposite electrode surface in response to the applied potential; and detecting L-glutamate in the subject based on the amperometric response signal.

10. The method of claim 9, wherein the biosensor is implanted in the subject.

11. The method of claim 10, wherein the subject is human.

12. The method of claim 9, further comprising measuring a level of L-glutamate in the subject based on the amperometric response signal.

13. The method of claim 12, further comprising determining a risk of traumatic spinal cord injury (SPI) based on the level.

14. The method of claim 13, further comprising treating the subject based on the level.

15. The method of claim 9, wherein said conductive polymer comprises poly(3,4-ethylenedioxythiophene) polystyrene sulfonate (PEDOT:PSS) and said flexible substrate comprises one or more of an Ecoflex polydimethylsiloxane (PDMS) composite and a liquid crystal polymer sheet (LCP).

16. The method of claim 15, wherein said platinum nanoparticles are 1% wt, said multiwall carbon nanotubes are 1% wt and said substrate Ecoflex PDMS composite is 16% wt.

17. The method of claim 9, wherein the nanocomposite electrode further comprises a layer of Nafion on its surface upon which the glutamate oxidase enzyme is immobilized.

18. The method of claim 9, wherein said applied potential is between 650 mV and −200 mV.

19. The method of claim 9, wherein the L-glutamate concentration is 12.85 nA $\mu M^{-1}$ $mm^{-2}$ or less.

20. The method of claim 9, wherein the subject has experienced a traumatic spinal cord injury (SPI).

* * * * *